United States Patent [19]

Cook et al.

[11] Patent Number: 4,647,659

[45] Date of Patent: Mar. 3, 1987

[54] CLAVULANIC ACID AMINE SALTS, THEIR PREPARATION AND USE

[75] Inventors: Michael A. Cook, Laughton, Nr Lewes; Alan D. Curzons, Brighton; Robert B. Wilkins, Worthing, all of England

[73] Assignee: Beecham Group p.l.c., England

[21] Appl. No.: 693,122

[22] Filed: Jan. 22, 1985

Related U.S. Application Data

[60] Continuation of Ser. No. 479,952, Mar. 29, 1983, abandoned, which is a division of Ser. No. 334,438, Dec. 24, 1981, Pat. No. 4,454,069, which is a continuation of Ser. No. 179,760, Aug. 20, 1980, abandoned.

[30] Foreign Application Priority Data

Aug. 24, 1979 [GB] United Kingdom ................ 7927544

[51] Int. Cl.$^4$ .............................................. C07D 487/04
[52] U.S. Cl. ..................................................... 540/349
[58] Field of Search ..................................... 260/245.3

[56] References Cited

FOREIGN PATENT DOCUMENTS 2733230  1/1978  Fed. Rep. of Germany ... 260/245.3
1578739 11/1980  United Kingdom ............ 260/245.3

Primary Examiner—Mark L. Berch
Attorney, Agent, or Firm—Jacobs & Jacobs

[57] ABSTRACT

This invention provides a novel process for the preparation of clavulanic acid and pharmaceutically acceptable salts and esters thereof which process utilizes the preparation of the tertiary-butylamine salt of clavulanic acid optionally in the form of an acetone solvate and subsequently converting said salt into the desired product.

3 Claims, No Drawings

CLAVULANIC ACID AMINE SALTS, THEIR PREPARATION AND USE

CROSS REFERENCE

This is a continuation of Ser. No. 479,952 filed Mar. 29, 1983, now abandoned, which is a division of Ser. No. 334,438 filed Dec. 24, 1981 now U.S. Pat. No. 4,454,069 which is a continuation of Ser. No. 179,760 filed Aug. 20, 1980, abn.

This invention relates to a novel process for the preparation of clavulanic acid of the formula (I):

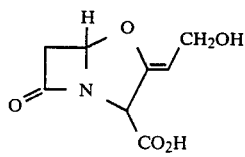

and pharmaceutically acceptable salts and esters thereof.

British Pat. No. 1508977 discloses inter alia that salts of clavulanic acid can be obtained by absorbing the clavulanate anion in filtered broth on to an anion exchange resin, eluting therefrom with an electrolyte, desalting the resulting solution, applying the desalted solution to a further anion exchange resin, chromatographically eluting therefrom with an electrolyte, desalting the resulting solution and thereafter removing the solvent. This process can be used to give acceptable yields of pure material but the use of resin columns involves significant investment and they can introduce limitations in large scale production operations, and so it would be desirable to have an alternative procedure available that involved few resin utilizing stages. British Pat. No. 1543563 discloses a process for the preparation of clavulanic acid salts via precipitation of lithium clavulanate.

It has now been found that the tertiary-butylamine salt of clavulanic acid which can be obtained in high purity is a useful intermediate in the preparation of clavulanic acid. The salt has been disclosed in Belgian Pat. No. 862211, but only as a suitable ingredient for pharmaceutical formulations.

The present invention provides the use of the tertiary-butylamine salt of clavulanic acid as an intermediate in the preparation of clavulanic acid and pharmaceutically acceptable salts and esters thereof.

In another aspect the present invention provides a process for the preparation of clavulanic acid or a pharmaceutically acceptable salt or ester thereof which process comprises converting the tertiary-butylamine salt of clavulanic acid into clavulanic acid or a pharmaceutically salt or ester thereof.

In a further aspect the present invention provides a process for the purification of clavulanic acid or a pharmaceutically acceptable salt or ester thereof which process comprises:

(i) contacting impure clavulanic acid in organic solvent with tertiary-butylamine, (ii) isolating the tertiary-butylamine salt of clavulanic acid, and (iii) converting the thus formed tertiary-butylamine salt into clavulanic acid or a pharmaceutically acceptable salt or ester thereof.

The pharmaceutically acceptable salts and esters of clavulanic acid prepared by the processes of this invention are those described in British Patent Specification Nos. 1508977 and 1508978 which are herein incorporated by reference.

Particularly suitable salts include the pharmaceutically acceptable alkali and alkaline earth metal salts, for example the sodium, potassium, calcium and magnesium salts. Of these salts the sodium and potassium are most suitable and the potassium is preferred.

Suitable esters include those cleavable to provide clavulanic acid or a salt thereof, by chemical methods such as hydrogenolysis or by biological methods.

Suitably the carboxylic acid is esterified by a group of the sub-formula (a), (b), (c) or (d):

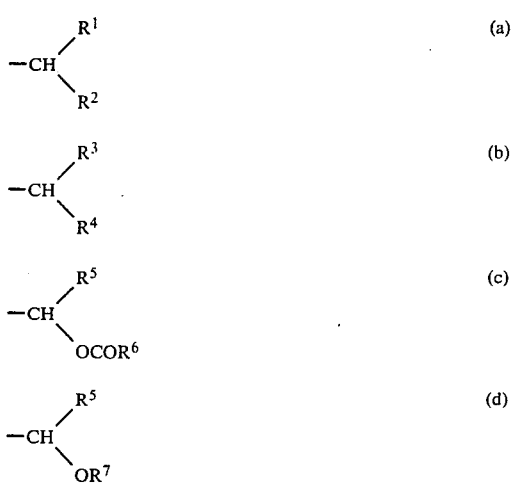

wherein $R^1$ ia a hydrogen atom or an alkyl, alkenyl or alkynyl group of up to 3 carbon atoms; $R^2$ is a hydrogen atom or a methyl group; $R^3$ is a phenyl group or a phenyl group substituted by a fluorine, chlorine or bromine atom or a nitro, methyl or methoxy group; $R^4$ is a hydrogen atom or a phenyl group or a phenyl group substituted by a fluorine, chlorine or bromine atom or a nitro, methyl or methoxy group; $R^5$ is a hydrogen atom or a methyl group; $R^6$ is a $C_{1-4}$ alkyl, phenyl or $C_{1-4}$ alkoxy group or $R^5$ is joined to $R^6$ to form a phthalidyl, dimethylphthalidyl or dimethoxyphthalidyl group; and $R^7$ is a $C_{1-4}$ alkyl, phenyl, chlorophenyl or nitrophenyl group; or $CHR^1R^2$ is a phenacyl or bromophenacyl group.

Favourably $R^1$ is a hydrogen atom or a methyl, ethyl, vinyl or ethenyl group. Favourably $R^2$ is a hydrogen atom. Favourably $R^3$ is a phenyl, p-bromophenyl, p-methoxyphenyl or p-nitrophenyl group. Favourably $R^4$ is a hydrogen atom. Favourably $R^6$ is a methyl, t-butyl or ethoxy group or is joined to $R^5$. Favourably $R^7$ is a methyl group.

Preferred groups of the sub-formula (a) include the methyl and ethyl groups.

Preferred groups of the sub-formula (b) include the benzyl and p-nitrobenzyl groups.

Preferred groups of the sub-formula (c) include the acetoxymethyl, pivaloyloxymethyl, α-ethoxycarbonyloxymethyl and phthalidyl groups.

A preferred group of the sub-formula (d) is the methoxymethyl group. The source of impure clavulanate material for use in this process may be any clavulanate producing micro-organism; liquors obtained by fermentation using such micro-organisms may be treated in conventional manner prior to solvent extraction, for example as described in British Patent Specification No. 1508977.

The tertiary-butylamine salt of clavulanic acid is obtained by contacting tertiary-butylamine (2-amino-2-methylpropane) with the clavulanic acid. This is conveniently performed by adding a solution of tertiarybutylamine in an organic solvent to a solution of impure clavulanic acid in an organic solvent.

The solution of clavulanic acid in organic solvent may be obtained by extraction of an acidified aqueous solution of clavulanic acid. Preferably the pH of the aqueous solution prior to extraction is in the range 1 to 3. Preferably the extraction is carried out at a temperature from 5° to 15° C. The aqueous solution should contain at least approximately 25 mg/ml, preferably approximately 100 mg/ml of clavulanic acid to give best results. The aqueous acidified solution for extraction may be conveniently obtained from a fermentation broth by acidifying an aqueous solution obtained by absorbing the clavulanate anion from the broth onto an anion exchange resin, eluting the clavulanate therefrom with an aqueous solution of an electrolyte, and optionally desalting.

Suitable organic solvents in which impure clavulanic acid is contacted with tertiary-butylamine include those of the formula (II):

wherein $R^8$ is a $C_{1-6}$ alkyl group or a $C_{1-6}$ alkoxy group and $R^9$ is a $C_{1-6}$ alkyl group. Further suitable solvents include ethers such as tetrahydrofuran and dioxan. The present invention also encompasses mixtures of such solvents.

More suitably the organic solvent is one which can be used directly to extract the acidified aqueous solution and may be selected from the group consisting of ethyl acetate, methyl acetate, propyl acetate, n butyl acetate, methyl ethyl ketone, methyl isobutyl ketone, tetrahydrofuran and mixtures of such solvents. Of these the most suitable are methyl isobutyl ketone, methyl ethyl ketone, and ethyl acetate. Suitable solvent mixtures include methyl ethyl ketone/methyl isobutyl ketone and tetrahydrofuran/methyl isobutyl ketone. A preferred solvent is ethyl acetate.

Suitable solvents for tertiary-butylamine include acetone, ethyl acetate, methyl isobutyl ketone, and methyl ethyl ketone. Of these acetone is preferred.

It has been found that the process is operable in presence of a small amount of water in the solvent or solvent mixture. Typically 0–7% (vol/vol) water may be present, preferably less than 4%. More suitably however the solution of the clavulanic acid is subjected to drying, for example over magnesium sulphate.

In general one equivalent of tertiary-butylamine or a slight excess thereof is used to produce the salt of clavulanic acid. The solutions are generally mixed slowly with stirring and the mixture stirred for some time after addition is complete. The desired tertiary-butylamine salt of clavulanic acid may then be isolated. In this way the tertiary-butylamine salt of clavulanic acid is separated from most or all of the impurities. This may be effected in conventional manner, for example by centrifugation with subsequent removal of the supernatant liquid.

In one preferred embodiment of this invention, the tertiary-butylamine clavulanate is employed as an acetone solvate. This acetone solvate has advantageous stability and purity characteristics compared to previously known forms of the tertiary-butylamine salt of clavulanic acid, see for example Belgian Pat. No. 862211. The solvate is particularly useful in the present invention because it can readily be isolated as a highly pure and stable crystalline compound.

Accordingly the present invention also provides the tertiary-butylamine salt of clavulanic acid in the form of an acetone solvate.

In the presence of acetone, the tertiary-butylamine salt of clavulanic acid precipitates in the form of an acetone solvate, comprising bound acetone at levels corresponding to hemi- or mono-solvation. During isolation and/or drying, some acetone may be lost since the strength of solvation is not high, but the amount of acetone in the product is not critical and in general varies up to 17% (w/w) (that is to say up to mono-solvation). We have found that the percentage of acetone in the solvate is suitably between 2%–9%, more suitably between 4%–8%, and preferably about 7%. It has been found that the percentage of acetone in the solvate may be greatly diminished by washing with organic solvent, for example methyl isobutyl ketone or ethyl acetate. However, it is difficult to remove the acetone content under vacuum indicating that a distinct chemical entity is present. The acetone solvate is formed by contacting clavulanic acid in organic solvent with tertiary-butylamine in the presence of acetone.

In general, a solution containing clavulanic acid is mixed with at least the same volume of acetone together with the tertiary-butylamine, when the salt is precipitated.

Preferably tertiary-butylamine dissolved in acetone is mixed with a solution of clavulanic acid in an organic solvent. Favoured organic solvents include ethyl acetate, tetrahydrofuran, methyl ethyl ketone, methyl isobutyl ketone and mixtures of such solvents, of which ethyl acetate is preferred. It is preferred that in order to form the desired acetone solvate the organic solvent:acetone ratio after mixing should be approximately 1:1.

Recrystallisation of the initial acetone solvate is often advantageous to further reduce the level of impurities. A convenient solvent for the recrystallisation is aqueous acetone. Such recrystallisation is performed in conventional manner, for example the solvate is dissolved in water, treated with a small amount of acetone, filtered, and then treated with larger volumes of acetone optionally with stirring and/or cooling to afford the recrystallised product.

The tertiary-butylamine salt of clavulanic acid optionally in the form of its acetone solvate may be converted into clavulanic acid or a pharmaceutically acceptable salt or ester thereof by ion-replacement or by esterification.

Such ion-replacement may be performed using ion-exchange resins, for example by passing a solution of the tertiary-butylamine salt through a bed of a cation exchange resin in sodium, potassium or calcium form.

Suitable cation exchange resins include Amberlite IR 120 and equivalent resins. Alternatively ion-replacement may be effected by metathesis of the tertiary-butylamine cation with a base, for example a carbonate, bicarbonate or hydroxide or pharmaceutically acceptable alkali or alkaline earth metal, or a salt of an organic carboxylic acid, for example a salt of an alkanoic acid of formula (III):

$$R^{10}\text{—}CO_2H \tag{III}$$

wherein $R^{10}$ is an alkyl group, containing for example from 1 to 20 carbon atoms, preferably from 1 to 8 carbon atoms. Examples of suitable salts include the acetate, propionate or ethylhexanoate salts, potassium 2-ethylhexanoate and sodium 2-ethylhexanoate being preferred.

Suitable methods of esterification include:
(a) the reaction of the tertiary-butylamine salt of clavulanic acid with a compound of the formula $Q\text{-}R^{11}$ wherein Q is a readily displaceable group and $R^{11}$ is an organic group;
(b) the reaction of the tertiary-butylamine salt of clavulanic acid with an alcohol or thiol in the presence of a condensation promoting agent such as carbodi-imide; and
(c) the reaction of the tertiary-butylamine salt of clavulanic acid with a diazo compound.

It is of course realised that the foregoing processes extend to cover those aspects wherein the tertiary-butylamine salt is first converted to clavulanic acid or other salt and subsequently is converted to the desired ester.

Further details of esterification methods are disclosed in British Patent Specification Nos. 1508977 and 1508978.

Use of the present invention enables salts and esters of clavulanic acid to be more readily obtained in pure form than operation of the processes of British Patent Specification Nos. 1508977 and 1543563. For example, one preferred product, potassium clavulanate, can be prepared in crystalline form by the methods of said patents but these crystals are microcrystals. However the present invention enables potassium clavulanate to be produced in pure form in large crystals which may be well-defined needles or waisted plates (i.e. butterfly-shaped).

The following Examples illustrate the invention:

EXAMPLE 1

An ethyl acetate extract obtained by known methods containing crude clavulanic acid (68 l assayed at 24.75 mg/ml) was stirred for 10 minutes with $MgSO_4$ (1.7 kg). Carbon (1.7 kg "Norrit GSX") was added and the mixture stirred for a further 10 minutes. The slurry was filtered by sucking through a fine-woven canvas filter (a Nutsche filter) which was then washed with ethyl acetate (10.1). The combined filtrate and washing (71 l total) contained 23.7 mg/ml of clavulanic acid in dry ethyl acetate. To this was added acetone (71 l) and then a solution of t-butylamine (1.13 l) in acetone (5.6 l) over 30 minutes. The mixture was stirred for 60 minutes and then the solid product separated by centrifugation and then washed with acetone (2×10 l) and finally dried on a fluid bed drier (ambient temperature) to yield the t-butylamine salt of clavulanic acid acetone solvate (2.25 kg), assaying at 65.8% free acid and 97% as T.B.A. clavulate acetone solvate. Yield corrected for purity, 88%. Infra-red (Nujol Mull) 1780 ($\beta$-lactam carbonyl), 1708 (solvated acetone), 1695 $cm^{-1}$ (C=C).

For comparison addition of free acetone to the above sample gave rise to an absorption at 1721 $cm^{-1}$ corresponding to free acetone, and the non-solvated t-butylamine salt of clavulanic acid shows no absorption at 1708 $cm^{-1}$.

EXAMPLE 2

Recrystallisation of t-butylamine Clavulanate Acetone Solvate

A sample of the product of Example 1 was dissolved in water to yield a 20% w/v solution (based on clavulanate ion) at ambient temperature. Acetone (8 vols) was added over about 10 minutes and the resulting solution filtered. To the filtrate is added further acetone (32 vols) over about 30 minutes and the resulting mixture stirred for a further 2 hours with chilling to 0°–5° C. The precipitate was filtered off and dried in a fluid bed drier to yield the t-butylamine salt of clavulanic acid acetone solvate. (assay 66.0% free acid, 99.7% T.B.A. clavulanate acetone solvate. Yield, corrected for purity, 85%). (The product of this Example was about 1–2% purer than the starting material).

EXAMPLE 3 t-Butylamine salt of clavulanic acid acetone solvate (2.55 kg) was dissolved in isopropanol (68 l) containing water (1.4 l) at 20° C. The solution was filtered through an in-line filter and washed through with isopropanol (2.1 l). Potassium ethyl hexanoate in isopropanol (1.4 equiv., 6.1 l of 2N solution) was added over 20 minutes. The resulting mixture was stirred for 30 minutes at ambient temperature and chilled for 2 hours to 0°–5° C. The product was filtered by suction through a fine-woven canvas filter (Nutsche) with nitrogen purge, washed with isopropanol (10 l) and acetone (10 l). The product was then dried under vacuum at ambient temperature to yield potassium clavulanate (1.8 kg). Assay 83.2%. Yield, corrected for purity, 89%.

EXAMPLE 4

The tertiary-butylamine salt of clavulanic acid (non-solvated) (28.7 g, 69.8% as pure free acid) was dissolved in isopropanol (760 ml) containing water (10–40 ml) at 20° C. The solution was filtered and washed through with further isopropanol (25 ml). Potassium ethyl hexanoate in isopropanol (71 ml of 2N solution, 1.4 equivalents) was added over 15 minutes. The resulting mixture was stirred for 30 minutes at ambient temperature and then chilled for 2 hours at 0°–5° C. The product was filtered, washed with isopropanl (100 ml) and acetone (100 ml). The product was then dried under vacuum at ambient temperature to yield potassium clavulanate (20.5 g, 81.2%), yield 83.0%.

What is claimed is:
1. The tertiary-butylamine salt of clavulanic acid in the form of an acetone solvate.
2. The salt of claim 1 having 4%–8% (w/w) acetone.
3. The salt of claim 1 having about 7% (w/w) acetone.

* * * * *